United States Patent
Funke et al.

(10) Patent No.: US 9,580,469 B2
(45) Date of Patent: Feb. 28, 2017

(54) PEPTIDES FOR THE TREATMENT AND EARLY DIAGNOSIS OF ALZHEIMER'S DISEASE AND OTHER TAUOPATHIES

(71) Applicant: FORSCHUNGSZENTRUM JUELICH GMBH, Juelich (DE)

(72) Inventors: Susanne Aileen Funke, Sonnefeld (DE); Dieter Willbold, Juelich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 14/432,802

(22) PCT Filed: Sep. 10, 2013

(86) PCT No.: PCT/DE2013/000520
§ 371 (c)(1),
(2) Date: Apr. 1, 2015

(87) PCT Pub. No.: WO2014/053110
PCT Pub. Date: Apr. 10, 2014

(65) Prior Publication Data
US 2015/0299259 A1    Oct. 22, 2015

(30) Foreign Application Priority Data

Oct. 5, 2012    (DE) .................. 10 2012 019 882

(51) Int. Cl.
| | | |
|---|---|---|
| C07K 7/08 | (2006.01) | |
| C07K 14/47 | (2006.01) | |
| C07K 7/06 | (2006.01) | |
| G01N 33/68 | (2006.01) | |
| A61K 38/00 | (2006.01) | |

(52) U.S. Cl.
CPC . *C07K 7/08* (2013.01); *C07K 7/06* (2013.01); *C07K 14/4711* (2013.01); *G01N 33/6896* (2013.01); *A61K 38/00* (2013.01); *G01N 2800/2821* (2013.01)

(58) Field of Classification Search
CPC ......... C07K 7/06; C07K 14/4711; C07K 7/08; G01N 33/6896; G01N 2800/2821; A61K 38/00
See application file for complete search history.

(56) References Cited

U.S. PATENT DOCUMENTS

2010/0204085 A1    8/2010  Eisenberg et al.

FOREIGN PATENT DOCUMENTS

| EP | 1 379 546 | 1/2004 |
|---|---|---|
| WO | WO-00/48621 | 8/2000 |
| WO | WO-01/18546 | 3/2001 |
| WO | WO-02/081505 | 10/2002 |

OTHER PUBLICATIONS

Sievers Stuart A et al: "Structure-based design of non-natural amino-acid inhibitors of amylid fibril formation", Nature: International Weekly Journal of Science (and SupplementaryInformation), Nature Publishing Group, United Kingdom, Bd. 475, Nr. 7354, Jul. 1, 2011 (Jul. 1, 2011), Seiten 96-100, XP001526382 ISSN: 0028-0836, DOI: 10.138/NATURE10154 in der Anmeldung erwacehnt das ganze Dokument.
Allal Boutajangout et al: "Passive immunization targeting pathological phospho-tau protein in a mouse model reduces functional decline and clears au aggregates from the brain", Journal of Neurochemistry, Bd. 118, Nr. 4, Aug. 1, 2011 (Aug. 1, 2011), Seiten 658-667, XP055081677, ISSN: 0022-3042, DOI: 10.1111/j.1471-4159.2011.07337.x das ganze Dokument.
Esteras-Chopo et al: "New Strategy for the Generation of Specific d-peptide Amyloid Inhibitors", Journal of Molecular Biology, Academic Press, United Kingdom, Bd. 377, Nr. 5, Jan. 16, 2008 (Jan. 16, 2008), Seiten 1372-1381, XP022551388, ISSN: 0022-2836, DOI: 10.1016/j.jmb.2008.01.028 das ganze Dokument.
Jing Zheng et al: "Macrocyclic [beta]-Sheet Peptides That Inhibit the Aggregation of a Tau-Protein-Derived Hexapeptide", Journal of The American Chemical Society, Bd. 133, Nr. 9, Mar. 9, 2011, Seiten 3144-3157, XP055095036, ISSN: 0022-7863, DOI: 10.1021/ja110545h das ganze Dokumeut.
Brunden KR, Ballatore C, Crowe A, Smith AB 3rd, Lee VM, Trojanowski JQ. Tau-directed drug discovery for Alzheimer's disease and related tauopathies: a focus on tau assembly inhibitors. EXP Neurol. Jun. 2010:223(2):304-10.
Sievers SA, Karanicols J., Chang HW, Zhao A, Jiang L., Zirafi O, Stevens JT, Muench J, Baker D, Eisenberg D. Structure-based design of non-natural amino-acid inhibitors of amyloid fibril formation. Nature Jun. 15, 2011;475(7354):96-100.
Temple F, Smith and Michael S. Waterman, (Advances in Applied Mathematics 2: 482-489; (1981) Comparison of Biosequences.
A General Method Applicable to the Search for Similarities in the Amino Acid Sequence of Two Proteins Saul B. Needleman and Christian D. Wunsch—J. Mol. Biol. (1970) 48, 443-453 pgs.
Roempp Chemie Lexikon (chemistry encyclopedia), 9th edition, vol. 1, p. 650 et seq. Georg Thieme Verlag, Stuttgart.
Assembly of τ protein into Alzheimer paired helical filaments depends on a local sequence motif ($^{306}$VQIVYK$^{311}$) forming β structure, PNAS, 1999. 97(10); p. 5129-5134 M. von Bergen et al.
Synergistic Interactions between Repeats in Tau Protein and AB Amyloids May be Responsible for Accelerated Aggregation via Polymorphic States, p. 5172-5181, 2011. 50(23); Yifat Miller et al.
Structure-based design of non-natural amino-acid inhibitors of amyloid fibril formation Stuart A. Sievers et al.—Jun. 15, 2011; vol. 475(7354): 96-100.

*Primary Examiner* — Gregory S Emch
(74) *Attorney, Agent, or Firm* — Jordan and Koda, PLLC

(57) ABSTRACT

The present invention relates to novel tau protein aggregate-binding peptides, homologs, fragments, parts and polymers thereof and to the use thereof.

10 Claims, 3 Drawing Sheets

Figure 1:
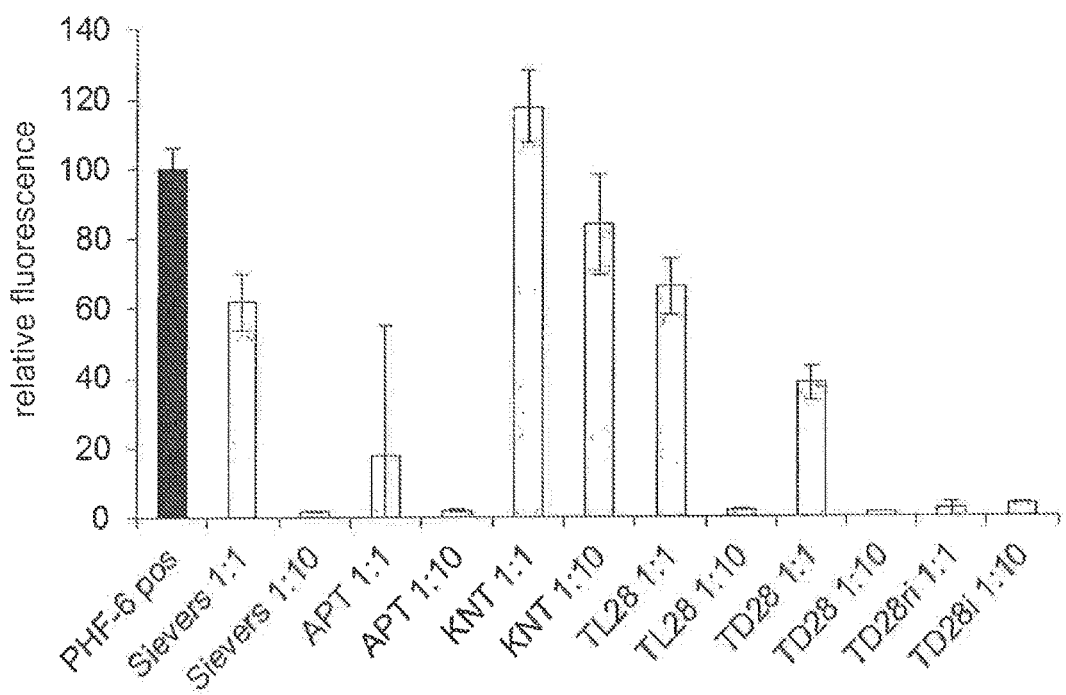

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: D-Peptid (TD28)

<400> SEQUENCE: 1

Thr Thr Ser Leu Gln Met Arg Leu Tyr Tyr Pro Pro
```

```
1               5                   10

<210> SEQ ID NO 2
<211> LENGTH: 12
<212> TYPE: PRT
<213> ORGANISM: Artificial Sequence
<220> FEATURE:
<223> OTHER INFORMATION: D-Peptid (TD28ri)

<400> SEQUENCE: 2

Pro Pro Tyr Tyr Leu Arg Met Gln Leu Ser Thr Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: D-Peptid (Apt)

<400> SEQUENCE: 3

Ala Pro Thr Leu Leu Arg Leu His Ser Leu Gly Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D-Peptid (Knt)

<400> SEQUENCE: 4

Lys Asn Thr Pro Gln His Arg Lys Leu Arg Leu Ser
1               5                   10
```

PEPTIDES FOR THE TREATMENT AND EARLY DIAGNOSIS OF ALZHEIMER'S DISEASE AND OTHER TAUOPATHIES

BACKGROUND OF THE INVENTION

The invention relates to peptides for the treatment and early diagnosis of Alzheimer's disease and other tauopathies.

Alzheimer's disease (AD) is characterized by the pathological aggregation of two proteins, the Aβ peptide (amyloid beta peptide, Abeta peptide) and the tau protein. Both kinds of protein aggregations are considered neurotoxic, while the respective monomers are not toxic or have important functions in vertebrate cells.

In vertebrate cells, the tau protein binds to supporting cytoskeleton proteins (microtubules) and regulates the assembly of the same. The group of tauopathies covers neurodegenerative diseases involving deposits of the tau protein. The most widely known tauopathy is Alzheimer's disease. However, pathological tau aggregates also occur in 17 other diseases, such as frontotemporal dementia and Parkinson's disease. In some instances, a mutated tau protein is the only main feature in terms of pathology.

Various isoforms of the tau protein can be found in the human central nervous system. Tau proteins can agglomerate and form abnormal "paired helical filaments" (PHF). As a result of these pathological changes, PHF deposits can be observed as neurofibrillary tangles in the brains of Alzheimer patients. Since aggregated tau proteins are no longer functional, the assembly of the microtubules is disrupted.

Small molecules that are intended to prevent tau protein aggregation were already described. However, they are low in numbers compared to molecules that are intended to prevent, or reverse, Aβ aggregation. Of late, since treating Alzheimer's by solely focusing on Aβ aggregates may not be able to produce the desired success, the tau protein and the interaction thereof with the Aβ peptide have been increasingly addressed in the literature. For example, reducing the plaque content through anti-Aβ immunotherapy has not resulted in the expected improvements in the cognitive capabilities of the treated patients. Many scientists meanwhile even ascribe a neuroprotective effect to Aβ.

Tau aggregation inhibitors and modulators can potentially complement existing therapeutic experiments. While the cause of the tau aggregation cascade remains unknown to this day, a close correlation exists between the number of neurofibrillary tangles in the neurons, cellular degeneration, and the symptoms of dementia.

Preliminary data from phase 2 clinical studies demonstrate that the inhibition of tau aggregation is useful for treating AD. Rhodanine-based inhibitors resulted in a clear reduction of tau aggregation-based cytotoxicity in the cytosol of neuronal cell models. In phase IIa clinical studies, AL-108, the intranasal formulation of the NAP peptide consisting of eight amino acids, was found to have a positive influence on the memory capacity of patients with amnestic mild cognitive impairment (aMCI). A direct influence on the hyperphosphorylation of tau was shown for NAP, among other things, initial studies substantiate successes after tau-based immunotherapy of transgenic mouse models. Tau-based therapies will play an ever greater role in the future, since tau aggregates have infectious properties. The pathological tau aggregation can be passed on from one cell to another. In addition, tau-expressing mouse models show a clearer pathology after artificial infection with tau aggregates.

In addition to therapeutic components, there is an urgent need for improved diagnostic methods for AD. So far, a variety of substances that bind to aggregated Aβ peptide exist. Following the incorporation of radionuclides into these substances, imaging methods such as positron emission tomography (PET) and single photon emission computed tomography (SPECT) can be carried on the live patent ("in vivo imaging"). Since the amount of plaque has little correlation with the progression of AD, substances that bind with high specificity to tau aggregates potentially provide a diagnostic alternative, since the occurrence of neurofibrillary tau tangles correlates with the progression of the disease. So far, only few substances have been described which selectively bind in vitro to the aggregated tau protein. Quinoline and benzimidazole derivatives selectively stained neurofibrillary tangles in brain sections of deceased AD patients.

The disadvantage is that, so far, only symptoms of AD can be treated. No approved medications exist which can stop or reverse the disease process. The majority of substances being explored for AD treatment focus on extracellular Aβ, but not on tau pathology or, preferably, on both.

SUMMARY OF THE INVENTION

There are no probes for in vivo imaging which bind specifically to tau aggregates and render these visible. Since tau aggregates play such an important and early role in the history of the disease, exactly this would be desirable, in contrast to Aβ plaques, the amount of tau deposits in the brain correlates with the progression of the disease.

It is the object of the invention to provide peptides that:
a) allow the cause of Alzheimer's disease or other tauopathies to be treated by preventing the formation of toxic tau aggregates or by detoxifying the same; or that
B) allow Alzheimer's disease or other tauopathies to be diagnosed by using the peptides as a probe for an in vivo imaging process.

According to the present invention, the object of the invention is achieved by peptides containing at least one amino acid sequence that binds to the full-length tau protein and the use thereof. The invention is also achieved by methods of using a kit and compositions including peptides of the invention.

A peptide of the invention containing an amino acid sequence that binds to the full-length tau protein is preferably a peptide according to SEQ ID NO: 1 (TD28), SEQ ID NO: 2 (TD28ri), SEQ ID NO: 3 (Apt) and/or SEQ ID NO: 4 (Knt) and homologs, fragments and parts thereof which also bind to the full-length tau protein.

The object is also achieved by polymers of SEQ ID NO: 1 (TD28), SEQ ID NO: 2 (TD28ri), SEQ ID NO: 3 (Apt) and/or SEQ ID NO: 4 (Knt) and/or the homologs thereof.

Fragments and parts exhibit a similar or identical effect as the peptides according to the invention.

In one variant, the peptides, in particular those according to SEQ ID NO: 1 (TD28), SEQ ID NO: 2 (TD28ri), SEQ ID NO: 3 (Apt) and/or SEQ ID NO: 4 (Knt) and the homologs thereof, are substantially composed of D-amino acids. Within the meaning of the invention "substantially composed of D-amino acids" shall mean that at least 80%, preferably 75% or 80%, particularly preferably 85%, 90% or 85%, and in particular 96%, 97%, 98%, 99% or 100% of the monomers to be used is D-amino acids. D-amino acids advantageously elicit a lower immune response than the corresponding L-amino acids.

A polymer within the meaning of the invention is formed of 2, 3, 4, 5, 8, 7, 8, 9, 10, 11, 12, 13, 14, 15, 18, 17, 18, 19, 20 or more monomers, selected from the group consisting of SEQ ID NO: 1 (TD28), SEQ ID NO: 2 (TD28ri), SEQ ID NO: 3 (Apt) and/or SEQ ID NO: 4 (Knt) and the homologs thereof, which independently already bind to the tau protein or fragments thereof. According to the invention, the polymers are composed of one monomer, or of a combination of 2, 3, 4, 5, 8, 7, 8, 9, or 10 different above-mentioned monomers. Monomers and polymers are hereinafter referred to as peptides according to the invention.

In one variant of the invention, a peptide is used having the amino acid sequence according to SEQ ID NO: 1, SEQ ID NO: 2, SEQ ID NO: 3 and/or SEQ ID NO: 4 and/or homologs thereof having an identity of 50%. Within the meaning of the invention, "homologous sequences" or "homologs" shall mean that an amino acid sequence has an identity of at least 50, 55, 60, 85, 70, 71, 72, 73, 74, 75, 78, 77, 78, 79, 80, 81, 82, 83, 84, 85, 88, 87, 88, 89, 90, 91, 92, 93, 94, 95, 98, 97, 98, 98 or 100% with one of the above-mentioned amino acid sequences of the monomers. Instead of the term "identify," the terms "homologous" or "homology" are used as synonyms in the present description. The identity between two nucleic acid sequences or polypeptide sequences is calculated by comparison with the aid of the BESTFIT program, based on the algorithm by Smith, T. F. and Waterman, M. S (Adv. Appl. Math. 2: 482-489 (1981)), setting the following parameters for amino acids: Gap creation penalty: 8 and Gap extension penalty: 2; and setting the following parameters for nucleic acids: Gap creation penalty: 50 and Gap extension penalty: 3. The identity between two nucleic acid sequences or polypeptide sequences is preferably defined by the identity of the nucleic acid sequence/polypeptide sequence over the entire respective sequence length, as it is calculated by comparison with the aid of the GAP program, based on the algorithm by Needleman, S. B. and Wunsch, C D, (J. Mol. Biol. 48: 443-453), setting the following parameters for amino acids: Gap creation penalty: 8 and Gap extension penalty: 2; and setting the following parameters for nucleic acids: Gap creation penalty: 50 and Gap extension penalty: 3.

Two amino acid sequences are identical within the meaning of the present invention if they have the same amino acid sequence.

In one variant, homologs shall be understood to mean the corresponding retro-inverse sequences of the above-mentioned monomers. According to the invention, the term "retro-inverse sequence" denotes an amino acid sequence that is composed of amino acids in the enantiomeric form (inverse: chirality of the alpha carbon atom is inverted), and in which additionally the sequence order was reversed compared to the original amino acid sequence (retro=reverse).

In a further variant, the peptides according to the invention also bind to parts of the tau protein and/or to the full-length tau protein, and in particular to the aggregate consisting of the tau protein.

In a further variant, the peptides according to the invention have sequences that differ from the indicated sequences by up to three amino acids. Moreover, peptides containing the above-mentioned sequences are also used as sequences.

In a further variant, the peptides comprise fragments of the above-mentioned sequences or comprise homologous sequences with respect to the above-mentioned sequences.

According to the invention, the peptide is a peptide for use in medicine, and preferably for treating Alzheimer's disease or other tauopathies.

A further variant concerns a peptide according to the invention for inhibiting fibril formation or aggregation of tau protein.

The peptides according to the invention prevent (further) aggregation of the tau protein by binding to monomers or smaller oligomers, or they detoxify polymers, and fibrils, formed of the tau protein by binding thereto, thus converting them into non-toxic compounds. The present invention thus also relates to a method for detoxifying polymers or fibrils formed of the tau protein.

In one embodiment, the invention also relates to peptides according to the invention that are linked to another substance. The linkage within the meaning of the invention is a chemical bond as it is defined in Römpp Chemie Lexikon (chemistry encyclopedia), 9th edition, volume 1, page 650 et seq. Georg Thieme Verlag, Stuttgart, preferably a principal valence bond, and more particularly a covalent bond.

The substances, in one variant, are pharmaceutical products or active ingredients, defined according to German Drug Act §2 or §4 (19), as amended in September 2012.

In one alternative, active ingredients are therapeutically active substances that are used as active pharmaceutical substances. Preferably anti-inflammatory agents are used.

In a further variant, the substances are compounds that enhance the effect of the peptides according to the invention. These may also be other peptides that bind to tau or Aβ, for example.

In one alternative, such compounds are aminopyrazole and/or aminopyrazole derivatives. Aminopyrazole derivatives within the meaning of the invention are 3-aminopyrazole-5-carboxylic acid or 3-nitropyrazole-5-carboxylic acid and all derivatives in which the heterocyclic CH group was replaced with —CR— or —N or —O— or —S—, and all peptidic dimers, trimers or tetramers derived therefrom, preferably aminopyrazole trimer.

In a further alternative, they are compounds that improve the solubility of the peptides and/or passage through the blood brain barrier.

In one alternative, the peptides according to the invention have any arbitrary combination of at least two or more features of the above-described variants, embodiments and/or alternatives.

The invention further relates to a peptide according to the invention for binding to aggregated tau proteins.

The invention moreover relates to a method for producing the peptide according to the invention by way of peptide synthesis, as known to a person skilled in the art, for example, organic synthesis methods for arbitrary low-molecular-weight compounds and/or mutagenesis and recombinant production.

The invention further relates to a composition, containing the peptide(s) according to the invention. In particular for treating Alzheimer's disease or other tauopathies.

The present invention further relates to a composition containing the peptide(s) according to the invention, in particular for preventing toxic tau protein aggregation.

The "composition" according to the invention can be a vaccine, a drug (such as in tablet form), an injection solution, a food or dietary supplement, for example, containing the peptide according to the invention in a formulation to be produced based on expert knowledge.

The invention further relates to a kit containing the peptide according to the invention.

In such a kit, the peptide(s) according to the invention can be packaged in containers, optionally with/in buffers or solutions. All components of the kit may be packaged in the same container or separately from each other. The kit can moreover include instructions for the use thereof. Such a kit can include, for example, the peptides according to the invention in an injection vial having a stopper and/or septum. A disposable syringe can also be included therein, for example.

The present invention further relates to the use of the peptide according to the invention as a probe for identifying and qualitatively and/or quantitatively determining tau proteins, preferably tau protein aggregates or fibrils.

The present invention further relates to a probe, containing the peptide(s) according to the invention for identifying and qualitatively and/or quantitatively determining tau protein, preferably tau protein aggregations or fibrils.

Such probes are of great importance in enabling early diagnosis of AD. Early diagnosis allows the disease to be counteracted at a very early stage.

Such molecular probes contain the peptide according to the invention and optionally dyes, fluorescent dyes, radioactive isotopes (PET and the like), gadolinium (MRI), and alternative substances suitable for the imaging of probes and can be injected in the patient, for example intravenously. After passing the blood brain barrier, the probes can bind to tau protein and/or deposits thereof. The tau proteins and/or deposits thereof thus marked can be rendered visible using imaging processes, such as SPECT, PET, CT, MRI, proton MR spectroscopy and the like.

The invention also relates to the use of the peptide for preventing tau aggregates and/or tau fibrils (tangles).

The peptide according to the invention is also used to detoxify toxic tau aggregates. It is used in particular to bind to tau protein and/or the aggregates thereof.

The invention further relates to the use of the peptide according to the invention as a therapeutic agent for treating Alzheimer's disease or other tauopathies.

The peptides according to the invention bind particularly well to tau protein and parts thereof, and preferably to tau aggregates and fibrils.

In one embodiment of the invention, the peptides have an increased ability to pass the blood brain barrier and/or increased solubility due to added sequences and arginine.

The peptides according to the invention very efficiently inhibit the formation of fibrils/aggregation of tau protein.

The peptides according to the invention moreover bind to tau protein, whereby amorphous aggregates are formed, as was verified by way of dynamic light scattering, these being negative in the ThT assay.

The invention further relates to the use of the peptides according to the invention in a method for treating (in vitro, ex vivo) blood, blood products and/or organs, characterized in that the blood, the blood products and/or the organs are derived from the human or animal body and tau proteins are removed and/or detoxified.

DETAILED DESCRIPTION OF THE INVENTION

The invention will be characterized in greater detail hereafter based on exemplary embodiments, without thereby limiting the invention.

Selecting tau-binding peptides:

In a mirror image phage display selection, D-enantiomeric peptides that bind to the aggregated tau protein were selected.

It was possible to generate multiple D-enantiomeric peptides that bind both to the aggregated tau partial peptide and to the aggregated full-length tau and inhibit the aggregation thereof, or result in a formation of amorphous aggregates.

In mirror image phage display selections, the selection rounds are carried out against a D-enantiomer as the target, which must be generated synthetically. Since this is not possible for the full-length tau protein (441 amino acids), the selections were carried out against the D-enantiomer of a 6-mer tau fragment (PHF-6), which can be found in tau repeats R2 and R3 and, according to various studies, forms the core of the neurofibrillary tangles (von Bergen, M., Assembly of τ protein into Alzheimer paired helical filaments depends on a local sequence motif (306VQIVYK311) forming β structure PNAS, 1999. 97(10): p. 5129-5134; Miller, M., Synergistic Interactions between Repeats in Tau Protein and Aβ Amyloids May Be Responsible for Accelerated Aggregation via Polymorphic States. 5172-5181, 2011. 50(23): p. 5172-5181). Since aggregated material is to serve as the target for the selection, and monomeric tau protein has important physiological functions and must not be inhibited in vivo, only fribriilary material was used for the selection. The quality of aggregation was checked using thioflavin T (ThT). ThT is a fluorescent dye that binds to structures of various amyloid proteins rich in β-pleated sheets and fluoresces after excitation at 440 nm. The emission can in this way be correlated with the relative fibril content in the sample. ThT assays are used to measure the fibrillization of Aβ and tau protein, and most notably with ligands, so as to defect a possible inhibitory effect of the same on Aβ or tau aggregation.

A phage display kit made by Biolabs was used for the following selections. At the same time, a regular phage display was carried out for the selection of L-peptides. In this regard, obtaining binding motifs after database searches allows conclusions to be drawn concerning previously unknown binding partners in vivo. Moreover, binding partners can later be tested as D-peptides or retro-inverso peptides. After selection, enriched phages were isolated and single-phage ELISA assays were carried out. Phages that in the single-phase ELISA showed clear binding to PHF-6 fibrils, but not to the blank well, were amplified, precipitated, and the DINA was isolated and sequenced. The D-peptides Apt and Knt stem from selections against D-PHF-8. Against L-PHF-6, a peptide having the sequence TTSLQMRLYYPP was selected, which we also analyzed in D-enantiomeric form (TD28) and as a retro-inverso peptide (TD28ri).

The following peptide sequences in particular achieve the object of the invention.

TD28: ttslqmrlyypp
TD28ri: ppyylxmqlstt
Apt: aptilrlhslga
Knt: kntpqhrklrls

While TD28 and TD28ri convert tau fibrils into large amorphous aggregates and thus possibly detoxify these, Apt and Knt dissolve existing tau fibrils.

A D-enantiomeric peptide that binds to the tau fragment PHF-8 was already described. It was found via in silico methods (sequence: tlkivw, Sievers et al., Nature. 2011 Jun. 15; 475(7354):96-100. doi: 10.1038/nature10154.). In our experiments, this peptide inhibited the aggregation of PHF-6 to a similar degree as that of the peptides we developed, but not the aggregation of the full-length tau protein.

Characterization of the inhibitory properties of the tau-binding peptides:

In the next step, the influence of the tau-binding peptides on the aggregation of tau was examined. For this purpose, the above-described ThT assay was used. The analyses were initially carried out with the PHF-6 fragment that was used for selection. A D-enantiomeric peptide was used for control purposes, which after the start of our work was described as a PHF-6-binding and aggregation-inhibiting peptide. It was generated via in silico methods (Sievers, K. Structure-based design of non-natural amino-acid inhibitors of amyloid fibril formation. Nature, 2011. 475: p. 96-100) and optimized for maximal effect. The generated peptides were used in ratios of 1:1 and 10:1 in relation to PHF-6. At the same time, the peptides were tested without PHF-6 (negative control for self-fibrillization) and PHF-6 without tau-binding peptides (positive control, maximal aggregation). As is shown in FIG. 1, ail peptides caused a dosage-dependent reduction in the fibril formation of PHF-6. Some peptides exhibited similarly strong inhibition of the fibrillization as the peptide that is known from the literature and described by Sievers et al.

Thereafter, whether the peptides inhibited not only the fibrillization of PHF-6, but also that of the full-length tau protein was examined. As can be seen from FIG. 2, all analyzed peptides inhibited the fibrillization of the full-length tau protein. All selected peptides thus inhibited the fibrillization better than the peptide selected by Sievers, which in most approaches showed no effect at all.

Figure 3:
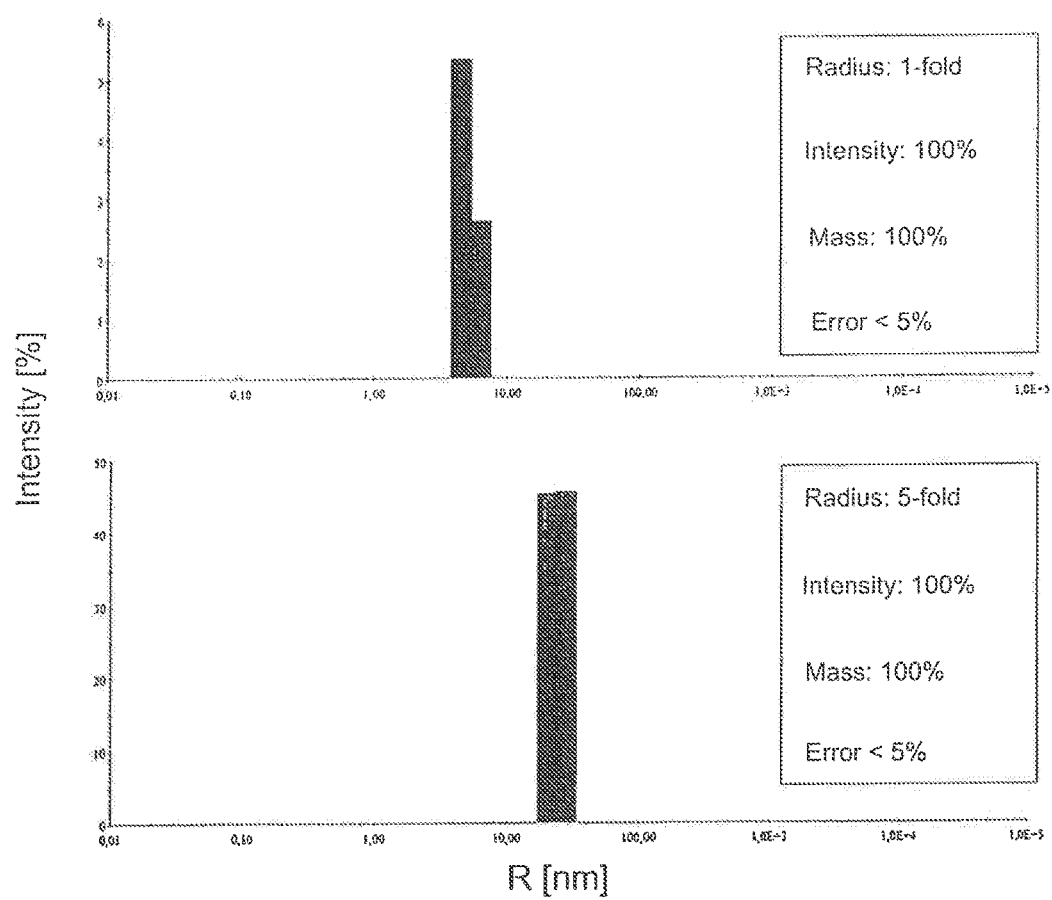

Since strong inhibition of the fibrillization of tau was observed for the selected peptides, measurements were additionally carried out using dynamic light scattering (DLS) so as to track aggregation in general, independently of the secondary structure of the particles. For this purpose, 1 μg/ml tau full-length protein was analyzed using 100 μM arachidonic acid and the respective peptide at a ratio of 1:10. Tau without peptide and without the addition of arachidonic acid was measured for control purposes. The latter was used as a negative control since Tau did not aggregate under the applied test conditions without arachidonic acid (FIG. 3). It was found that some of the peptides prevented the aggregation of tau over the measured test period, while other peptides (TD28 and TD28ri) resulted in the formation of very large aggregates (see Table 1). The fact that no ThT-positive fibrils were detectable in the ThT assay under the same concentration conditions indicates that the peptide-induced particles were not fibrillary aggregates, but amorphous and presumably non-toxic aggregates. A similar mechanism was already shown for the peptide D3 from EP 1 379 546 B1, which converts toxic Aβ oligomers into non-toxic, amorphous aggregates. The peptide selected by Sievers et al. showed no effect on the aggregation of the full-length tau protein.

TABLE 1

Results summary of the DLS measurements with tau and various peptides. Tau without the addition of arachidonic acid (AA) exhibited no tendency to aggregate. Incubation of Tau with AA resulted in aggregation and a 5-fold increase in particle size.

| Sample | Particle size Day 1 | Mass Day 1 | Particle size Day 8 | Mass Day 8 |
| --- | --- | --- | --- | --- |
| Tau | 1-fold | ≥99% | 1-fold | ≥98% |
| Tau + AA | 5-fold | 100% | 4-fold | 100% |
| Tau + AA + Sievers | 6-fold | 100% | 6-fold | ≥98% |
| Tau + AA + APT | 1-fold | ≥99% | 1-fold | ≥98% |
| Tau + AA + KNT | 1-fold | ≥99% | 1-fold | ≥99% |
| Tau + AA + LPS | 1-fold | ≥99% | 1-fold | ≥99% |
| Tau + AA + D3 | 1-fold | 100% | 1-fold | 100% |
| Tau + AA + TL28 | 5-fold | ≥99% | 4-fold | 100% |
| Tau + AA + TD28 | 42-fold | 100% | 48-fold | 100% |
| Tau + AA + TD28ri | 55-fold | 100% | 44-fold | 100% |

In the drawings:

FIG. 1 shows a ThT aggregation assay of PHF-6 for quantifying the relative fibril content in the presence of different PHF-6-binding peptides. The concentration of PHF-6 was 25 μM; the peptides were measured at a ratio of 1:1 and 1:10 (PHF-6:peptide) and as controls individually in a 25 μM concentration (not shown). The fluorescence of 25 μM PHF-6 after two hours of incubation was set at 100%, and the values and standard deviations of the remaining incubations are indicated as percentages of this maximal value.

Figure 2:
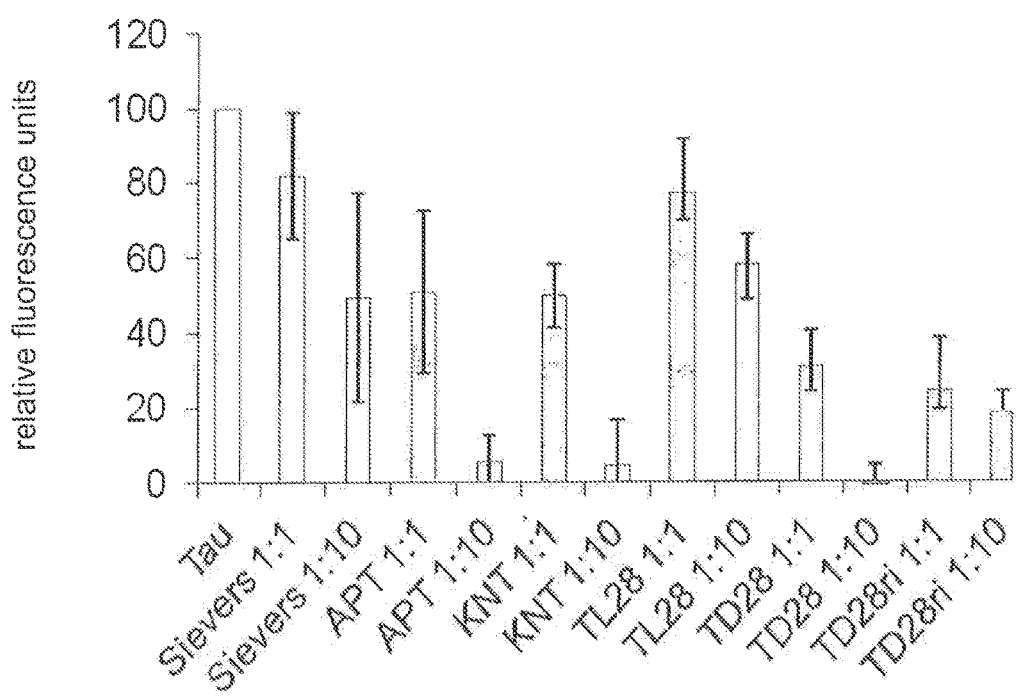

FIG. 2 shows a ThT aggregation assay of tau for quantifying the relative fibril content in the presence of different PHF-6-binding peptides and 100 μM arachidonic acid. The concentration of tau was 5 μM; the peptides were added at a ratio of 1:1 and 1:10 (tau:peptide). The fluorescence of 5 μM tau after 24 hours of incubation was set at 100%, and the values and standard deviations of the remaining incubations are indicated as percentages of this maximal value.

FIG. 3 shows DLS measurements of tau after 8 hours of incubation without (top) and with (bottom) the addition of 100 μM arachidonic acid, Tau was dissolved in PBS buffer to a concentration of 1 mg/ml. DLS was carried out with an acquisition time of 5 seconds for 3 minutes at room temperature.

The invention claimed is:

1. A peptide, artificially synthesized using either one or both of (i) an organic synthesis method and (ii) mutagenesis with recombinant production, which binds to a full-length tau protein and comprises the amino acid sequence of at least one of SEQ ID NO: 1, SEQ ID NO: 2, SEQ ID NO: 3, and SEQ ID NO: 4.

2. A peptide, artificially synthesized using either one or both of (i) an organic synthesis method and (ii) mutagenesis with recombinant production, which binds to a full-length tau protein and comprises the amino acid sequence of one of SEQ ID NO: 3 and SEQ ID NO: 4.

3. The peptide of claim 2, further comprising a second amino acid sequence, which comprises at least one of SEQ ID NO: 1 and SEQ ID NO: 2.

4. The peptide protein of claim 1 in which the at least one amino acid sequence is configured to bind to the full-length tau protein in a person having tauopathy so as to treat the tauopathy.

5. The peptide protein of claim 1 comprised of D-amino acids.

6. The peptide protein of claim 1 in which the at least one amino acid sequence is configured to bind to said tau protein and fibrils thereof so as to inhibit fibril formation of tau protein.

7. The peptide protein of claim 1 in which the at least one amino acid sequence is configured to hind to aggregated tau protein.

8. A kit, comprising a peptide protein of claim 1.

9. A probe for identifying and quantitatively and/or qualitatively determining tau protein, the aggregates thereof and/or tau fibrils, comprising the peptide protein of claim 1 and a substance suitable for imaging the probe.

10. A peptide, artificially synthesized using either one or both of (i) an organic synthesis method and (ii) mutagenesis with recombinant production, which comprises at least one amino acid sequence that is: at least 75% identical to SEQ ID NO: 1, at least 75% identical to SEQ ID NO: 2, at least 76% identical to SEQ ID NO: 3, or at least 80% identical to SEQ ID NO: 4.

* * * * *